(12) United States Patent
Huck et al.

(10) Patent No.: US 12,733,837 B2
(45) Date of Patent: Sep. 15, 2026

(54) DEVICE AND METHOD FOR DETERMINING A RESPIRATION RATE OF A SUBJECT

(71) Applicant: KONINKLIJKE PHILIPS N.V., Eindhoven (NL)

(72) Inventors: Salina Marie Huck, Boeblingen (DE); Andreas Wolfgang Schlack, Tübingen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 616 days.

(21) Appl. No.: 18/034,476

(22) PCT Filed: Oct. 20, 2021

(86) PCT No.: PCT/EP2021/079024

§ 371 (c)(1),
(2) Date: Apr. 28, 2023

(87) PCT Pub. No.: WO2022/090008

PCT Pub. Date: May 5, 2022

(65) Prior Publication Data

US 2024/0341619 A1 Oct. 17, 2024

(30) Foreign Application Priority Data

Oct. 28, 2020 (EP) .................................... 20204452

(51) Int. Cl.

| | |
|---|---|
| ***A61B 5/08*** | (2006.01) |
| ***A61B 5/00*** | (2006.01) |
| ***A61B 5/024*** | (2006.01) |

(52) U.S. Cl.

CPC ........ *A61B 5/0816* (2013.01); *A61B 5/02416* (2013.01); *A61B 5/725* (2013.01); *A61B 5/7257* (2013.01)

(58) Field of Classification Search

CPC ... A61B 5/0816; A61B 5/02416; A61B 5/725; A61B 5/7257

See application file for complete search history.

(56) References Cited

U.S. PATENT DOCUMENTS

| | | |
|---|---|---|
| 9,943,267 B2 | 4/2018 | Ferber |
| 2009/0326388 A1 | 12/2009 | Watson |

(Continued)

FOREIGN PATENT DOCUMENTS

| | | |
|---|---|---|
| EP | 2687154 A1 | 1/2014 |
| WO | 2006097866 A1 | 9/2006 |

OTHER PUBLICATIONS

Charlton Peter H et al: "Breathing Rate Estimation From the Electrocardiogram and Photoplethysmogram: A Review", IEEE Reviews in Biomedical Engineering, vol. 11, 2018, pp. 2-20, XP011687571, ISSN: 1937-3333, DOI: 10.1109/RBME.2017.2763681.

(Continued)

*Primary Examiner* — Abid A Mustansir

(57) ABSTRACT

The present invention relates to a device, system and method for determining a respiration rate of a subject. The device presented comprises an input interface for obtaining a red and/or an infrared photoplethysmography, PPG, signal, a feature signal unit configured to extract a first sequence of features from the PPG signal and to generate a first feature signal from said sequence of features, a resampling unit configured to resample with a resampling function the first feature signal to yield a resampled signal with a constant sampling rate and/or to resample a first derivative to yield a resampled first derivative with a constant sampling rate, a transformation unit configured to calculate a Fourier transform of the resampled signal to yield a transformed resampled signal or to calculate a Fourier transform of the resampled first derivative to yield a transformed resampled (Continued)

first derivative, and an extraction unit configured to extract from the transformed resampled signal a first respiration rate or from the transformed resampled first derivative the first respiration rate, wherein the first sequence of features is a sequence of phases of the first harmonic of a heart beat of the subject with respect to a start of the heart beat and wherein the first feature signal corresponds to the sequence of phases.

19 Claims, 11 Drawing Sheets

(56) References Cited

U.S. PATENT DOCUMENTS

2013/0079606 A1* 3/2013 McGonigle ........ A61B 5/14551 600/323
2013/0079657 A1* 3/2013 Ochs .................... A61B 5/7235 600/529
2015/0230759 A1 8/2015 Ochs
2016/0051205 A1 2/2016 Al-Ali
2016/0287090 A1 10/2016 Al-Ali
2017/0273635 A1* 9/2017 Li ........................ A61B 5/7278
2018/0103896 A1* 4/2018 Shin ..................... A61B 5/6824
2019/0357850 A1* 11/2019 Li .......................... A61B 5/721

OTHER PUBLICATIONS

International Search Report Dated Dec. 21, 2021 for International Application No. PCT/EP2021/079024 Filed Oct. 20, 2021.

* cited by examiner

DEVICE AND METHOD FOR DETERMINING A RESPIRATION RATE OF A SUBJECT

CROSS-REFERENCE TO PRIOR APPLICATIONS

This application is the U.S. National Phase application under 35 U.S.C. § 371 of International Application No. PCT/EP2021/079024, filed on Oct. 20, 2021, which claims the benefit of European Application No. 20204452.5 filed on Oct. 28, 2020. These applications are hereby incorporated by reference herein.

FIELD OF THE INVENTION

The present invention relates to a device, system and method for determining a respiration rate of a subject.

BACKGROUND OF THE INVENTION

Vital signs of a person generally serve as indicators of the current state of a person and as powerful predictors of serious medical events. Particularly, the respiratory system is known to adapt readily to demands placed on it. For this reason the respiration rate of a subject can be used as an indicator of clinical deterioration and physiological conditions such as hypoxia, hypercapnia and metabolic or respiratory acidosis, for example. Accordingly, an accurate measurement of the respiration rate may facilitate early treatment.

To allow for a precise measurement of the respiration rate diverse methods have been developed. Among others photoplethysmography, PPG, may be used to determine the respiration rate of a subject.

PPG is an optical measurement technique that evaluates a time-variant change of light reflectance or transmission of an area or volume of interest. PPG is based on the principle that blood absorbs light more than surrounding tissue, so variations in blood volume with every heart beat affect transmission or reflectance correspondingly. Therefore, the PPG waveform comprises information about the heart rate, but also information attributable to respiration, particularly the respiration rate, may be inferred from a PPG signal. By evaluating transmittance and/or reflectivity at different wavelengths (typically red and infrared), also the (arterial) blood oxygen saturation, often called SpO2, can be determined.

PPG, and calculating an SpO2-value from the PPG signal is state of the art and has been computed for decades. In early days it has been observed that often the respiration rate is visible within the raw PPG signal, however it was not always clearly visible in the so called pleth signal (which is the inverted and filtered raw wave signal).

In order to gain a more precise determination of the respiration rate, many different approaches have been developed.

US 2016/0051205 A1, for example, discloses systems and methods for using multiple physiological parameter inputs to determine multiparameter confidence in respiratory rate measurements. The system and method disclosed are based on taking the raw PPG waveform as an input.

SUMMARY OF THE INVENTION

It is an object of the present invention to provide a device, system and method for determining a respiration rate of a subject. In particular, it is an object to determine the respiration rate from a PPG signal with a high level of confidence.

In a first aspect of the present invention a device for determining a respiration rate of a subject is presented as claimed in claim 1.

In a further aspect of the present invention a system for determining a respiration rate of a subject is presented, the system comprising:

- a PPG sensor configured to provide a red and/or infrared photoplethysmography, PPG signal, and
- a device for determining a respiration rate of a subject.

In yet further aspects of the present invention, there are provided a corresponding method and a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and medium have similar and/or identical preferred embodiments as the claimed device, in particular as defined in the dependent claims and as disclosed herein.

The present invention is based on the idea to use the most meaningful features in a PPG signal, in particular in raw waves (PPG data), i.e. not in the pleth signal (which is the inverted and filtered raw wave signal), to determine the respiration rate of a subject. Since the raw waves are not filtered, they generally comprise more (useful) information than the pleth signal. Surprisingly, the inventors found that extracting a signal describing the phases of the first harmonic of heart beats with respect to the start said heart beats from the (raw) PPG signal may serve as reliable basis for determining the respiration rate of a subject. The first feature can thus represent a phase position of the first harmonic of the respective heart beat signal with respect to a start of said heart beat. The first feature signal may thus provide an indication of how said first feature, i.e. the phase position of the first harmonic, changes over time for a sequence of heart beats. The inventors have found that the change of phase position over time can be used as a reliable basis for determining a respiration rate of the subject.

In a first step, the device is configured to analyze the red and/or an infrared PPG signal obtained by the input interface and to look for pulse triggers, i.e. starting points of pulses/heart beats. In order to do so commonplace algorithms may be used. Preferably each heart beat is analyzed and judged for validity based on the history and the current perfusion, pulse and/or SpO2-value of the individual beat of the subject.

For all (valid) beats, all samples of the beats from the beginning to the end of a beat may be looked at. Optionally offset or drift removal may be applied, for example by subtracting a fit through the first and last sample of a beat, i.e. a straight line. Then a Fourier transform of the beat may be analyzed. The Fourier transform is calculated by the feature signal unit, for example. The phase and pulse start can be determined on a pulse-by-pulse basis. The feature signal unit then extracts for all beats the phase of the first harmonic of the respective beats in relation to a start of said beats, resulting in a sequence of phases of first harmonics in relation to the start of the beats. This sequence of features generates a first feature signal. It is extracted from the PPG signal by the feature signal unit.

Since the first feature signal describes a sequence of phases of the first harmonic of heart beats with respect to a start of these heart beats, its sample position depends on the (variable) sequence of the hearts of the subject. In fact, for each point in time where a beat is detected there is one measurement value, i.e. one measurement value per heart beat. Naturally, the heart beat frequency is not constant and so is the sample position and thus the sampling rate. To gain a constant sampling rate, the device may comprise a resampling unit configured to resample the first feature signal. Resampling yields a feature (i.e. phase of the first harmonic of a heart beat of the subject in relation to a start of the heart beat) vs. time signal with a constant sampling rate. Hence, resampling facilitates a subsequent Fourier transformation, for example. Preferably, the first feature signal is resampled with a resampling function. Subsequently, the extraction unit extracts from the transformed resampled signal, i.e. transformed resampled first feature signal corresponding to the sequence of phases of first harmonics of heart beats in relation to the heart beat starts, a first respiration rate.

In an embodiment the device further comprises an analyzing unit, wherein the extraction unit is configured to extract from the transformed resampled signal at least one further first respiration rate and wherein the analyzing unit is configured to determine from the two first respiration rates a most probable respiration rate.

In general, the respiration rates may be calculated by using different calculation methods. Accordingly, the at least two first respiration rates may differ. The analyzing unit then determines from said respiration rates, which have been calculated in different manners, a most probable respiration rate, i.e. a respiration rate which comes closest the true respiration rate of the subject. The analyzing unit may be a conventional data processing unit. However, the analyzing unit may likewise be a neural network. The neural network may be trained with training data, wherein said training data may be data already processed in the past or simulated data.

In an embodiment the feature signal unit is configured to extract a second sequence of features from the PPG signal and to generate a second feature signal from said second sequence of features, wherein the extraction unit is configured to extract from the second feature signal at least a second respiration rate, wherein the second feature signal is based on any of (a) an amplitude (of the processed PPG signal) at the base frequency of the subject's heart beats times pulse width of the heart beats, (b) an amplitude (of the processed PPG signal) at the base frequency of the heart beat, (c) single pulse perfusion, (d) pulse rate, (e) amplitude ratio of the base frequency and the first harmonic of the beat, (f) pulse amplitude variability, (g) pulse width variability and (h) surface of the beat.

Preferably, the second sequence of features comprises a sequence of amplitudes at the base frequency of the subject's heart beats times pulse width of said beats. To extract the amplitude at the base frequency of a heart beat all (infrared or red) raw wave samples from the beginning to the end of a single beat are taken. As described above, offset or drift removal may be applied, e.g. by subtracting a straight line, such as a fit through the first and last sample of the beat. Subsequently, there is calculated by the feature signal unit, for example, a Fourier transform of the single beat, resulting in the amplitude at the base frequency of said beat. In this approach the number of points in the Fourier transform varies with the length of the pulse. For example, with a sample rate of 125 Hz and a valid pulse-rate-range between 29.3 to 300 beats per minute (bpm), the number of samples of a single beat varies between 25 and 256 samples.

The tables below show results based on experimental data from several studies (2019, 2014, 2018) as to which different feature signals may provide the most promising results with respect to determination of a respiration rate of a subject. In Study3 (2018), for example, almost 500 files have been analyzed. The criteria used to determine which feature signals offer the best result are NPI=a+b and NPI2=2*a+b, wherein NPI2 is the better criterion of these two. Generally, the smaller NPI or NPI2, the better. The parameter "a" increases with increasing difference of the determined respiration rate from the reference value, whereas the parameter "b" takes a fixed value if the algorithm cannot determine a respiration rate and is otherwise zero. Since displaying a wrong value is worse than displaying no value, the part "a" is emphasized in NPI2. It is shown in the last columns in the tables, respectively. The lower the corresponding number, the better the result, i.e. the closer is the determined most probable respiration rate to the true respiration rate.

| Study1 (2019) Feature 1 | clinical Data Feature 2 | 346 min NPI = a + b | 10 Files a | NPI2 = 2*a + b |
|---|---|---|---|---|
| amp * pulse length | pulse rate | 3.772 | 0.25 | 4.022 |
| amp * pulse length | phase | 3.782 | 0.166 | 3.948 |
| amp * pulse length | perf | 3.677 | 0.282 | 3.959 |
| PAV | PWV | 3.931 | 0.364 | 4.295 |
| PAV | surface | 3.841 | 0.412 | 4.253 |
| surface | PWV | 3.815 | 0.283 | 4.098 |

| Study2 (2014) Feature 1 | clinical Data Feature 2 | 6844 min NPI = a + b | 24 Files a | NPI2 = 2*a + b |
|---|---|---|---|---|
| amp * pulse length | pulse rate | 2.507 | 1.543 | 4.05 |
| amp * pulse length | phase | 2.407 | 1.431 | 3.838 |
| amp * pulse length | perf | 2.65 | 1.67 | 4.32 |
| PAV | PWV | 3.482 | 2.364 | 5.846 |
| PAV | surface | 2.729 | 1.87 | 4.599 |
| surface | PWV | 3.244 | 2.132 | 5.376 |

| Study3 (2018) Feature 1 | clinical Data Feature 2 | 606 min NPI = a + b | 471 Files a | NPI2 = 2*a + b |
|---|---|---|---|---|
| amp * pulse length | pulse rate | 2.546 | 0.908 | 3.454 |
| amp * pulse length | phase | 2.281 | 0.702 | 2.983 |
| amp * pulse length | perf | 2.374 | 0.831 | 3.205 |
| PAV | PWV | 3.008 | 1.214 | 4.222 |
| PAV | surface | 2.729 | 1.146 | 3.875 |
| surface | PWV | 2.466 | 0.922 | 3.388 |

In the tables above, "PAV" refers to pulse amplitude variability, "PWV" refers to pulse width variability, "amp" refers to amplitude at the base frequency, "perf" refers to single pulse perfusion, "phase" refers to phase of the first harmonic of a beat and "surface" refers to the surface of a beat, i.e. the area spanned between the raw PPG signal and a straight line (not necessarily a horizontal line) from a maximum of a beat to the maximum of a following beat (see FIG. 13).

As can be seen, in all studies a combination of phase of the first harmonic of a heart beat of the subject with respect to a start of said heart beat with amplitude at the base frequency of the subject's heart beats times pulse width, i.e. pulse length, of said beats provides the best results.

However, the second feature signal may likewise be based on single pulse perfusion, which is calculated based on a combination of red and infrared PPG signals. To be more precise, single pulse perfusion is calculated in analogy to Patent WO 2006/097866 A1 but based on the red and infrared amplitudes of the fundamentals of a single beat.

A sequence of pulse rates may also be used as second feature signal. Preferably, the pulses of a person may be extracted based on an infrared PPG signal.

By the amplitude ratio of the fundamental and the first harmonic of a beat, the ratio of the amplitude of the processed PPG signal at the base frequency and the first harmonic of the beat is meant.

The pulse amplitude can be calculated by subtracting from the maximum of a beat the minimum of said beat for each beat. The pulse amplitude variability can be determined based thereon indicative of a variability of the pulse amplitudes.

Likewise, the pulse width variability can be determined by comparing the widths of beats in a sequence. The width of a single beat is determined by calculating the distance between the start and the end of a beat.

The surface of a beat is defined as the area spanned between the raw PPG signal and a straight line (not necessarily a horizontal line) from a maximum of a beat to the maximum of a following beat (see FIG. 13).

In this embodiment the analyzing unit may be configured to determine from the two first respiration rates (and the at least one second respiration rate) the most probable respiration rate. However, further first or second respiration rates may be determined and therefore also a most probable respiration rate thereof.

In another embodiment the device further comprises a calculation unit configured to calculate the first derivative of the first feature signal. Likewise, the first derivative of a second feature signal may be calculated.

Concerning the resampling unit the second feature signal or a derivative of the second feature signal may be resampled by a resampling function. The extraction unit may be configured to extract from the resampled first derivative a first respiration rate.

In another embodiment the device further comprises a filter unit configured to filter the resampled signal to yield a filtered resampled signal, wherein the extraction unit is configured to extract from the filtered resampled signal the first respiration rate, and/or to filter the resampled first derivative to yield a filtered resampled first derivative, wherein the extraction unit is configured to extract from the filtered resampled first derivative the first respiration rate. Similarly, the resampled second feature signal and/or the resampled first derivative of the second feature signal may be filtered and a second respiration rate may be determined.

In a preferred embodiment of the device, the filter unit is configured to filter adaptively in accordance with an expected respiration rate corresponding to the resampled signal and/or the resampled first derivative. For example, an adaptive low-pass filter may be applied to the first feature signal (and/or the second feature signal). The cut-off frequency of the low-pass filter may be at the expected respiration rate plus 5 respiration rates per minute, for example, wherein the expected respiration rate is preferably derived by the extraction unit from the (unfiltered) amplitude of the processed PPG at the base frequency of the subject's heart beats times pulse width of the heart beats. However, the cut-off frequency of the low-pass filter may also be higher or lower.

The transformation unit may be configured to calculate a Fourier transform of a resampled second feature signal (and/or a Fourier transform of a resampled first derivative of the second feature signal), wherein the extraction unit is configured to extract from said signal(s) the second respiration rate. Preferably, the extraction unit comprises two sub-units, wherein a first sub-unit is configured to extract a respiration rate from a signal in the time-domain and wherein a second sub-unit is configured to extract one or more respiration rates from a signal in the frequency domain.

In another embodiment the device further comprises a scoring unit configured to assign a score to the at least two first respiration rates describing the probability of the first respiration rates to represent the true respiration rate of the subject, wherein the analyzing unit is configured to determine the most probable respiration rate using said scores. Similarly, the scoring unit may also be configured to assign a score to the second respiration rates, wherein the analyzing unit is configured to compare the scores corresponding to the first and second respiration rates separately or to compare the scores of the first respiration rates also with the scores of the second respiration rates to determine the most probable respiration rate.

In yet another embodiment the device comprises a grouping unit configured to group the at least two first respiration rates into groups of similar respiration rates, wherein similarity is assumed if respiration rates differ by less than a predetermined rate difference, in particular wherein said predetermined rate difference is no more than two respirations per minute. However, the predetermined respiration rate difference may be higher or lower, as well. If no group within the given predetermined rate difference window exists, there is created a new group. The output of the grouping unit has at least two groups. Similarly, the grouping unit may be configured to group the second respiration rates into such groups as well (either separately or mixed with the first respiration rates).

In a preferred embodiment of the device, the grouping unit is further configured to add the scores of the at least two first respiration rates in a group to yield a group score, wherein the analyzing unit is configured to determine the most probable respiration rate from the group with highest group score. Preferably, the grouping unit generates at least two groups (per feature signal) and determines their corresponding group scores. Those two groups with the highest scores are then provided to the analyzing unit which is configured to determine the most probable respiration rate from said groups. However, the grouping unit may also be configured to add the scores of the second respiration rates in a group, or if there exist mixed groups, to add the scores of the first and second respiration rates of a group, to yield a group score, and the analyzing unit may be configured to determine the most possible respiration rate from the group with the highest group score.

In another preferred embodiment of the device, the analyzing unit is further configured to determine a confidence value for the most probable respiration rate based upon the number of respiration rates and the group score of the corresponding group, i.e. the group the most probable respiration rate belongs to. In particular, said confidence value is based on a comparison of the number of respiration rates and the group score in the group of the most probable respiration rate with the number of respiration rates and the group score of a second group (or even further groups). To be more precise, the confidence value is based on the differences between the group sizes and group scores. If the scores and/or sizes among the different groups are similar, the resulting confidence value is small. If one group is dominant, however, the confidence value is high. The confidence value (or a therewith calculated other value, e.g. a signal quality indicator) may then be used by clinical staff as an indicator of how reliable the most probable respiration rate is. For example, even if a respiration rate put out is the most probable one, its confidence value may be low. In this case, the most probable respiration rate does not represent the true respiration rate in a reliable manner.

The analyzing unit may likewise determine a second most probable respiration rate and a third most probable respiration rate and so on (either solely based on a group score or also based on the number of respiration rates in a group).

In yet another embodiment the first feature signal covers a time span of at least 60 seconds. However, the time span may likewise be shorter and may dynamically be adjusted, depending on the stability of the signal. A shorter time span may particularly be used to get a higher score for a particular respiration rate, for example. Alternatively, the first feature signal does not cover a particular time span, but a particular (predetermined) number of heart beats. The same may apply for the second feature signal.

All units of the device mentioned above may be used to process the first feature signal, but may likewise be used to process the second feature signal in the same manner. In fact, further feature signals may be extracted from the PPG signal by the feature signal unit, the further feature signals describing the same or other features as the first and/or second feature signals.

BRIEF DESCRIPTION OF THE DRAWINGS

These and other aspects of the invention will be apparent from and elucidated with reference to the embodiment(s) described hereinafter. In the following drawings.

DETAILED DESCRIPTION OF THE INVENTION

Figure 1:
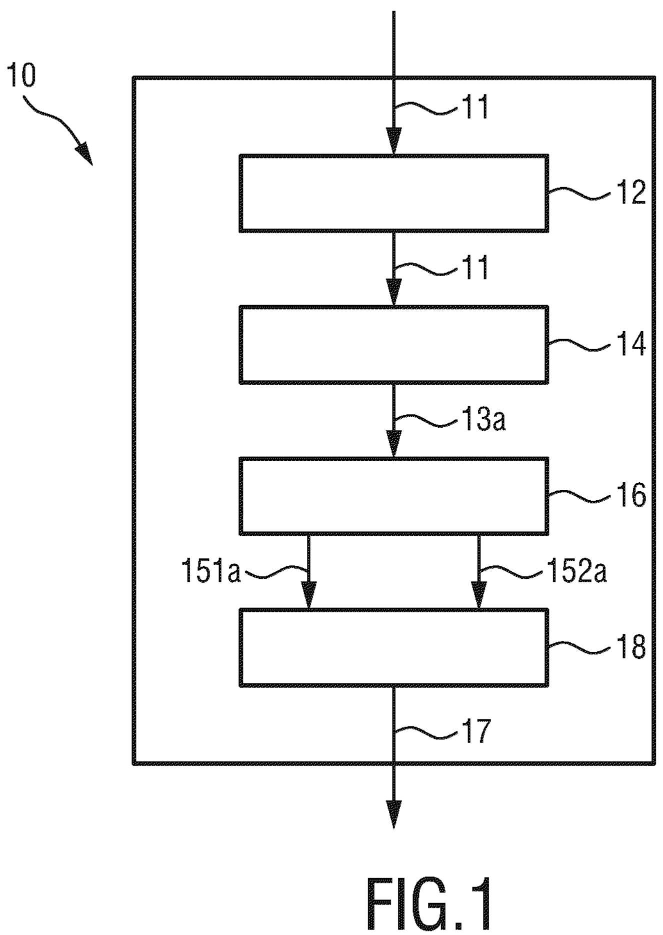
FIG. 1 shows a schematic diagram of a first embodiment of a device for determining a respiration rate of a subject according to the present invention.

FIG. 1 shows a schematic diagram of a first embodiment of a device 10 for determining a respiration rate of a subject according to the present invention. The device 10 comprises an input interface 12, a feature signal unit 14, an extraction unit 16 and optionally an analyzing unit 18. The input interface 12 is configured to obtain a red and/or an infrared PPG signal 11 from a PPG sensor attached to a patient, for example. The feature signal unit 14 analyzes the obtained PPG signal and extracts a first sequence of features from said signal. In particular, there is extracted the heart beats from the signal and for said heart beats there is determined a phase of the first harmonic of a heart beat of the subject with respect to a start of said heart beat. These phases in relation to the beats' starts represent a sequence of features and the feature signal unit generates a first feature signal from said sequence. From the first feature signal 13*a* the extraction unit 16 extracts at least a first respiration rate 151*a*. Optionally, the extraction unit 16 may extract a further respiration rate 152*a*. In a preferred embodiment there are extracted three or four first respiration rates. From the one or more respiration rates the analyzing unit may then, in an optional subsequent step, determine a highly possibly respiration rate group comprising at least one highly probable respiration rate. Preferably, there may also be determined an unlikely respiration group comprising at least one respiration rate being less likely than the at least one highly probable respiration rate.

Figure 2:
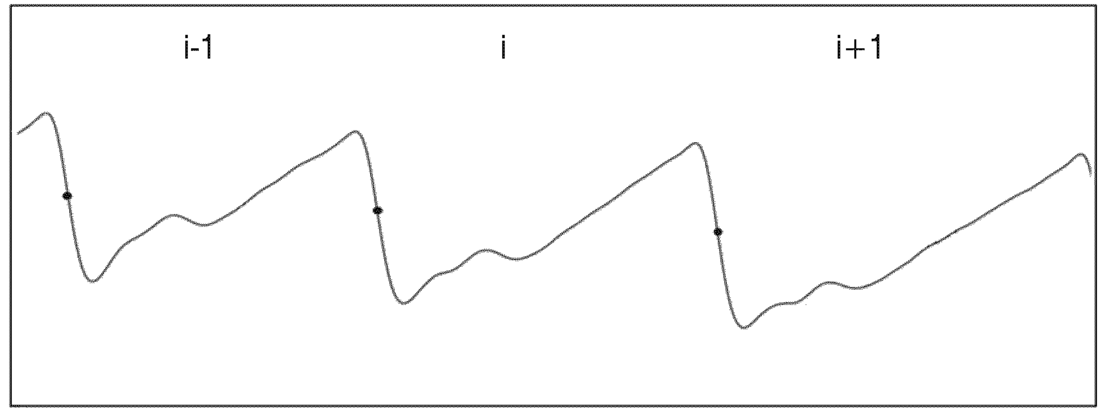
FIG. 2 shows a diagram of a beat-to-beat signal as derived from an infrared and/or red PPG signal according to the present invention.

FIG. 2 shows a diagram of a beat-to-beat signal as derived from an infrared and/or red PPG signal. A similar beat-to-beat signal could be derived from the infrared or red PPG signal only. The signal shows three beats, a first beat i−1, a second beat i and a third beat i+1. The dots shown in the signal are marking the pulse-triggers for each beat, i.e. the start for each beat. The pulse-triggers are calculated as highest slope of the falling edges shown in the diagram. In fact, the device 10 of the present invention, preferably the feature signal unit 14 of the device 10, is configured to look for said pulse triggers in the PPG signal. This way, the starting time of the beats is known and a phase of the first harmonic of a beat can be computed with respect to a start of the beat. The start of the heart beat can e.g. be determined based on a curve characteristic such as a maximum or minimum, turning point, maximum slope or the like.

Figure 3A:
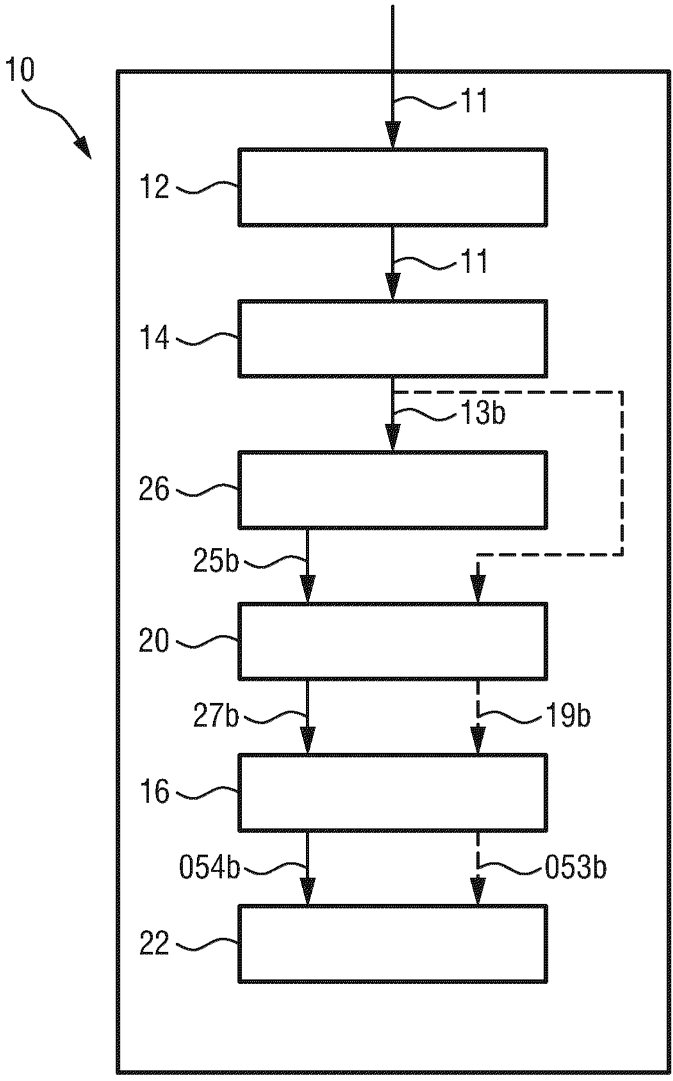
FIG. 3A shows a schematic diagram of a second embodiment of a device for determining a respiration rate of a subject according to the present invention.

FIG. 3A shows a schematic diagram of a second embodiment of a device for determining a respiration rate of a subject. In this embodiment the device 10 is configured to calibrate the cut-off frequencies of the filter unit 22. The device 10 comprises an input interface 12, a feature signal unit 14, a calculation unit 26, a resampling unit 20, a filter unit 22 and an extraction unit 16. The feature signal used for calibration preferably is the second feature signal, more preferably the amplitude of the processed PPG at the base frequency of subject's heart beats times the corresponding pulse width. In FIG. 3A signals bypassing the calculation unit 26 correspond to dashed lines (this also applies for FIGS. 3B and 4.

A third second respiration rate 053*b*, also referred to as second respiration rate three is determined by first resampling the second feature signal 13*b* as generated by the feature signal unit 14 from the incoming PPG signal 11. Resampling is performed by the resampling unit 20. The resampling can e.g. be performed with a trapezoidal resampling function. The resampled (first feature) signal 19*b* is then provided to the extraction unit 16 which derives a third second respiration rate 053*b*. Optionally, a further second respiration rate may be derived from said signal.

A fourth second respiration rate 054*b*, also referred to as second respiration rate four, is determined by first providing the second feature signal 13*b* to the calculation unit 26, which calculates a first derivative 25*b* of the first feature signal 13*b*. Subsequently, the resampling unit 20 resamples said first derivative 25*b* and thus generates a resampled first derivative 27*b* comprising a constant sampling rate. The resampled first derivative 27*b* is then provided to the extraction unit 16 which is configured to extract a fourth second respiration rate 054*b*.

Hence, in this embodiment the second respiration rates are determined from signals in the time domain.

Subsequently, said respiration rates are used to determine the cut-off frequencies for the filters in the filter unit 22. In particular, the third second respiration rate 053*b* is used to configure, i.e. calibrate, a band-pass filter, whereas the fourth second respiration rate 054*b* is used to configure, i.e. calibrate, a low-pass filter.

Figure 3B:
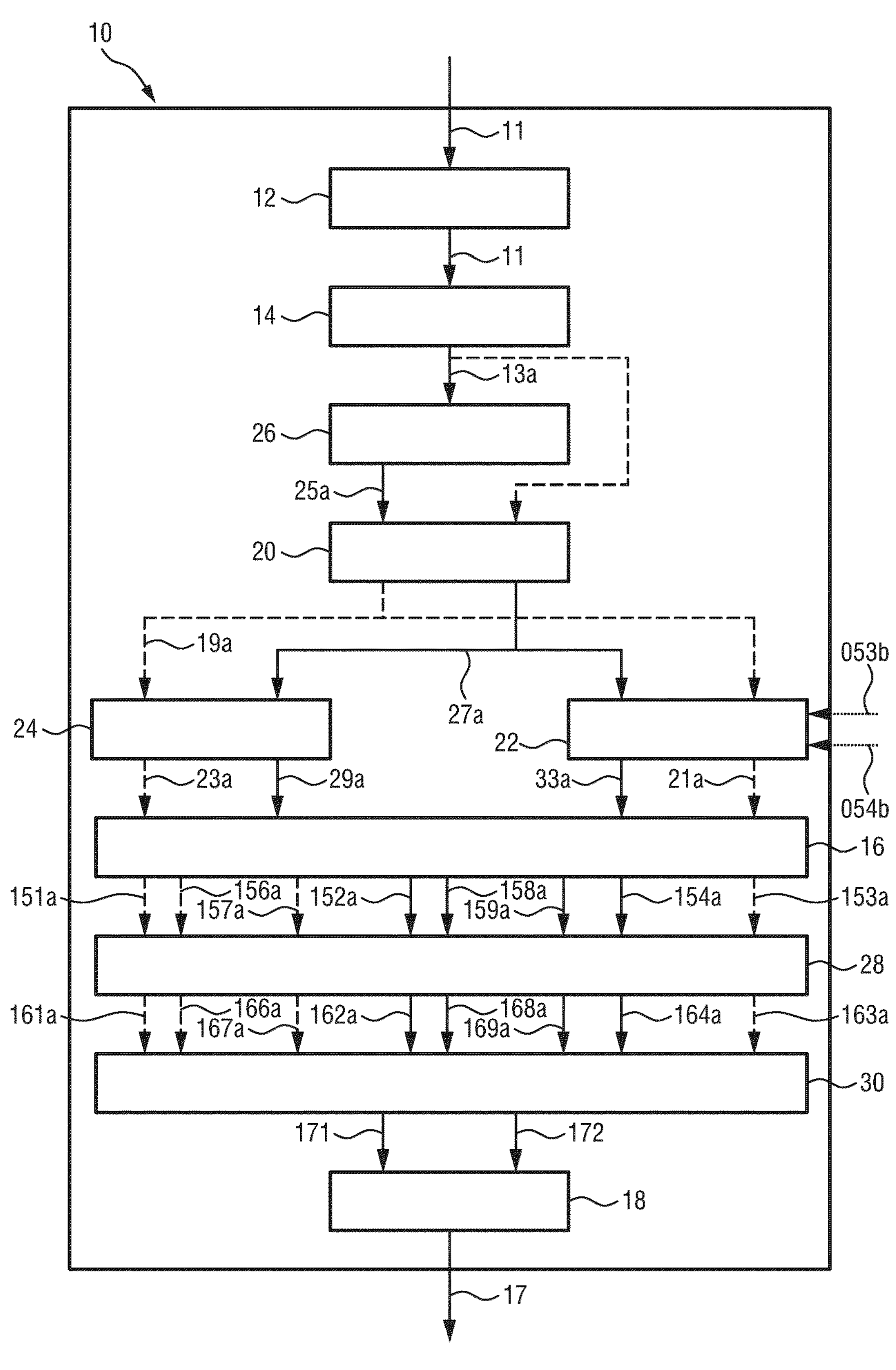
FIG. 3B shows a schematic diagram of a third embodiment of a device for determining a respiration rate of a subject according to the present invention

FIG. 3B shows a schematic diagram of a third embodiment of a device for determining a respiration rate of a subject. The device 10 comprises an input interface 12, a feature signal unit 14, a calculation unit 26, a resampling unit 20, a filter unit 22, a transformation unit 24, an extraction unit 16, a scoring unit 28, a grouping unit 30 and an analyzing unit 18.

A first first respiration rate 151*a*, also referred to as first respiration rate one, is determined by first resampling the first feature signal 13*a* as generated by the feature signal unit 14 from the incoming PPG signal 11. Resampling is performed by the resampling unit 20. The resampled (first feature) signal 19*a* is then provided to the transformation unit 24 which is configured to calculate a Fourier transform of the resampled signal 19*a*, i.e. to generate a Fourier transformed resampled signal 23*a*. The Fourier transformed resampled signal 23*a* is then provided to the extraction unit 16 which derives a first first respiration rate 151*a* from said signal. Accordingly, the first first respiration rate 151*a* is determined in the frequency domain. There may also be determined further first respiration rates from said signal, for example a sixth and seventh first respiration rate 156*a* and 157*a*, respectively.

A second first respiration rate 152*a*, also referred to as first respiration rate two, is determined by first providing the first feature signal 13*a* to the calculation unit 26, which calculates a first derivative 25*a* of the first feature signal 13*a*. Subsequently, the resampling unit 20 resamples said first derivative 25*a* and thus generates a resampled first derivative 27*a* comprising a constant sampling rate. The resampled first derivative 27*a* is then Fourier transformed by the transformation unit 24, resulting in a transformed resampled first derivative 29*a*. Using the resampled first derivative 29*a* the extraction unit 16 extracts a second first respiration rate 152*a*. Accordingly, also the second first respiration rate 152*a* is determined from a signal in the frequency domain.

A third first respiration rate 153*a*, also referred to as first respiration rate three, can optionally be extracted using the resampling unit 20 and the filter unit 22. In a first step the first feature signal 13*a* is resampled by the resampling unit 20 and then filtered by the filter unit 22, which generates a filtered resampled signal 21*a*. In this embodiment, the filter unit 22 is adapted to the (upper limit of the) expected respiration rate which is preferably derived from an (unfiltered) second feature signal, e.g. from a sequence of amplitudes at the base frequency of the subject's heart beats times pulse widths of the heart beats (see FIG. 3A). From the filtered resampled signal 21*a* the extraction unit 16 determines a first respiration rate three 153*a*. That is, the filtered resampled signal 21*a* is analyzed in the time-domain in this embodiment.

A fourth first respiration rate 154*a*, also referred to as first respiration rate four, can optionally be extracted using the calculation unit 26, which calculates a first derivative 25*a* of the first feature signal 13*a*, the resampling unit 20 and the filter unit 22. After calculation of the first derivate, the corresponding signal 25*a* is provided to the resampling unit which is configured to generate resampled first derivative 27*a*. After filtering the resampled first derivative, i.e. generating a filtered resampled first derivative 33*a*, the extraction unit 16 determines a first respiration rate four 154*a* from the filtered resampled first derivative 33*a*. That is, the filtered resample first derivative 33*a* is analyzed in the time-domain in this embodiment.

As to extraction of respiration rates 153*a* and 154*a*, the filter unit 22 may optionally further be provided with respiration rates 053*b* and 054*b* as determined, for example, in another device or in a prior calibration step as described with respect to FIG. 3A. The respiration rates 053*b* and 054*b* may particularly be used for filter calibration. However, filter calibration may also be performed in advance.

Generally, the extraction unit 16 is configured to extract further first respiration rates from signals in the frequency domain. Preferably, the extraction unit 16 does not only extract first respiration rate one and two, respectively from the Fourier transformed resampled signal 23*a* and the resampled first derivative 29*a*, but may further extract first respiration rates 156*a*, 157*a*, 158*a* and 159*a* as shown in FIG. 3B.

The extraction unit 16 may be divided into two sub-units, wherein a first (extraction) sub-unit is configured to process signals in the time domain and wherein a second (extraction) sub-unit is configured to process signals in the frequency domain. Accordingly, in this embodiment a first extraction sub-unit may be configured to extract the first respiration rates 153*a* and 154*a*, and a second extraction sub-unit may be configured to extract the first respiration rates 151, 152*a*, 156*a*, 157*a*, 158*a* and 159*a*.

The first respiration rates are processed further by the scoring unit 28. The scoring unit 28 assigns a score to each of the respiration rates, resulting in scored respiration rates 161*a*, 162*a* and so on. The scores assigned describe the probability of the respiration rates 151*a*, 152*a* and so on to represent the true respiration rate of the subject. For this purpose, the scoring unit 28 may be indicative of a quality metric for each of the first respiration rates. That is, the higher the score of a respiration rate, the higher the probability of said rate to be the true respiration rate. In particular with respect to low respiration rates, respiration rates which are determined from derivatives in the frequency domain are more reliable than those which are determined from derivatives in the time domain. Hence, a respiration rate extracted from a derivative in the frequency domain may be assigned a higher weight than a respiration rate extracted from a derivative in the time domain. The respective weights may then influence a score of the respiration rates.

Furthermore, for signals in the frequency domain, if there is a prominent peak, the score of the corresponding respiration rate is generally high. However, the spectrum exhibits several peaks it is not apparent which peak belongs to the correct respiration rate. Hence, the score is also dependent on the prominence of the highest peak and the height of the peak in relation to other peak heights.

The scored first respiration rates 161*a*, 162*a* and so on are then provided to the grouping unit 30 which is configured to group the respiration rates into groups of similar respiration rates. In this embodiment, the respiration rates are sorted into at least two groups, a first group 171 with a high group score, and a second group 172 with a lower group score. Subsequently, both groups 171 and 172 are provided to the analyzing unit 18 to extract the most probable respiration rate 17. In general, the respiration rate with the highest score is selected by the analyzing unit 18 to be the most probable respiration rate 17.

Figure 4:
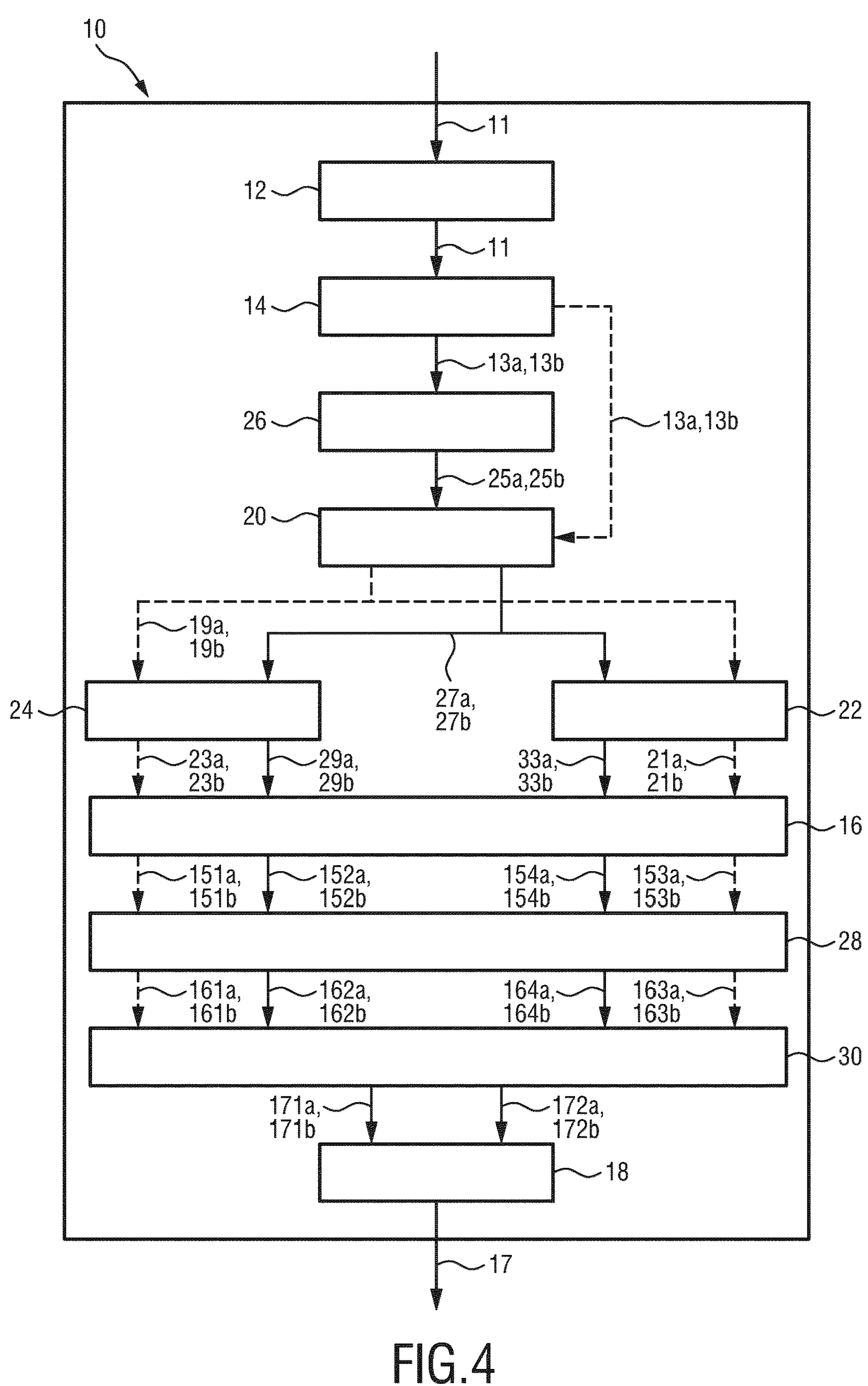
FIG. 4 shows a schematic diagram of a fourth embodiment of a device for determining a respiration rate of a subject according to the present invention.

FIG. 4 shows a schematic diagram of a fourth embodiment of a device for determining a respiration rate of a subject. The fourth embodiment comprises the same units as the third embodiment. Furthermore, in this embodiment, the feature signal unit 14 is configured to generate from the PPG signal 11 a first feature signal 13*a* and a second feature signal 13*b*. While the first feature signal 13*a* may comprise a sequence of phases of the first harmonic of beats of the subject in relation to starts of these beats, the second feature signal 13*b* may comprise a sequence of amplitudes at the base frequency of the subject's heart beats multiplied with the pulse widths of these beats. However, it is also conceivable, that the first feature signal 13*a* comprises a sequence of amplitudes at the base frequency of the heart beat and the second feature signal 13*b* comprises a sequence of single pulse perfusions. In any case, the feature signal 13*b* is processed just as the feature signal 13*a* in this embodiment. In particular, in this embodiment four first respiration rates 151*a*, 152*a*, 153*a* and 154*a* are determined and four second respiration rates 151*b*, 152*b*, 153*b* and 154*b* are determined.

First respiration rate one 151*a* and second respiration rate one 151*b* are determined in the same manner as first respiration rate one 151*a* in the third embodiment. First respiration rate two 152*a* and second respiration rate two 152*b* are determined in the same manner as first respiration rate two 152*a* in the third embodiment and the rates 153*a* and 153*b* and 154*a* and 154*b* are determined in the same manner as first respiration rate three 153*a* and the first respiration rate four 154*a*, respectively, in the third embodiment.

In summary, there are extracted four pairs of respiration rates, wherein two pairs are extracted from signals in the frequency domain and wherein two pairs are extracted from signals in the time domain.

The respiration rates are provided to the scoring unit 28 which assigns a score to the rates. The higher the score corresponding to a respiration rate, the higher the probability of said rate to be the true respiration rate. After obtaining the respiration rates and the corresponding scores the grouping unit 30 groups the respiration rate in different groups. In particular, respiration rates of the first respiration rates 151*a*, 152*a*, 153*a* and 154*a* are grouped together if they do not differ more than a predetermined respiration rate difference, for example, two respirations per minute (rpm). In the same way, the second respiration rates 151*b*, 152*b*, 153*b* and 154*b* are grouped. The scores of all respiration rates in a group are then summed up (by the grouping unit) and preferably also weighted to yield a group score. This way, the grouping unit provides the analyzing unit 18 with four groups 171*a*, 171*b*, 172*a* and 172*b*, for example, and with their corresponding group scores. In the analyzing unit 18 the group scores are analyzed and the group with the highest group score is assumed to comprise the most probable respiration rate. The most probable respiration rate 17 is the rate which appears most in the group with the highest group score in this embodiment. However, there are also other ways conceivable to determine the most probable respiration rate 17.

In fact, the most probable respiration rate 17 may not only be selected from the group with the highest group score, but also the number of respiration rates in a group may play a role. For example, if a group score is high, but there is only one respiration rate in the respective group, the most probable respiration rate 17 may be selected from another group with a higher number of respiration rates.

There also may be determined most probable respiration rates 17 corresponding, respectively, to the first respiration rates and the second respiration rates. The most probable respiration rate candidates of all features may then be clustered, resulting in a final respiration rate. Based on this step, also a confidence value may be calculated. Preferably, the confidence value is based on the differences between the group sizes and weights. If the weights and/or sizes among the different groups are similar, the confidence value is small. If one group is dominant, however, the confidence value is high. With respect to the final respiration rate there may also be derived a signal quality index. The signal quality index may be based on the confidence level of the final respiration rate and on the history of the output values.

Apart from that, the grouping unit 30 may also group the first and the second respiration rates into groups irrespective of their affiliation to a particular feature signal. Hence, in a group first and second respiration rates may also be mixed.

With respect to the first and second respiration rates, the analyzing unit 18 of the device 10 may also be used to determine second most probable respiration rates (together with their respective corresponding group size and group weight) or a second most probable respiration rate with respect to both kinds of respiration rates, i.e. all features of the PPG signal extracted.

Figure 5:
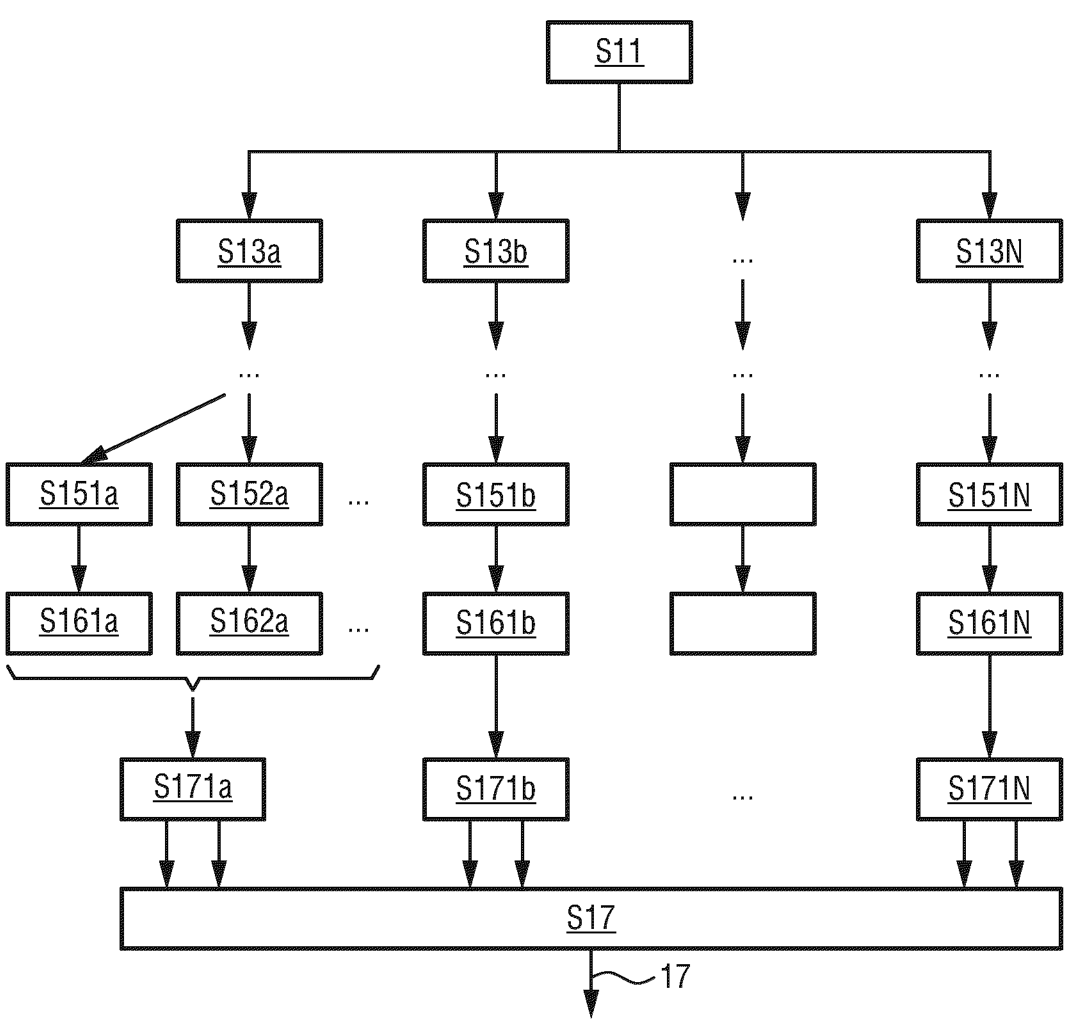
FIG. 5 shows a first schematic diagram of a method for determining a respiration rate of a subject according to the present invention.

FIG. 5 shows a first diagram of a method for determining a respiration rate of a subject according to the present invention. The method comprises a step S11 of providing a PPG signal from which in steps S13*a*, S13*b*, . . . , S13N N (different) feature signals are determined. The N feature signals may then be Fourier transformed or derived in an intermediate step, which is optional and not shown in the figure. In steps S151*a*, S152*a*, . . . S151*b*, S152*b*, . . . , S151N, S152N . . . at least one respiration rate is extracted from each of the N processed feature signals. Preferably, from signals in the frequency domain there are extracted at least two respiration rates. Accordingly, for each feature there may be extracted a plethora of respiration rates. Likewise, only one respiration may be extracted if a feature is only considered in the time domain. In steps 161*a*, 162*a*, . . . , 161*b*, 162*b*, 163*b*, . . . , 161N, 162N, . . . there is assigned a score to the feature signals. In steps S171*a*, S171*b*, . . . , S171N the scored respiration rates for each feature signal are grouped into different groups. In this embodiment, there are generated two groups per feature signal. Particularly, for each feature (signal) a group with a high group score, and a group with a lower group score is generated. However, there could also be generated further groups of respiration rates with a similar score. In step S17 it is decided in the analyzing unit which respiration rate is the most probable respiration rate 17.

Figure 6:
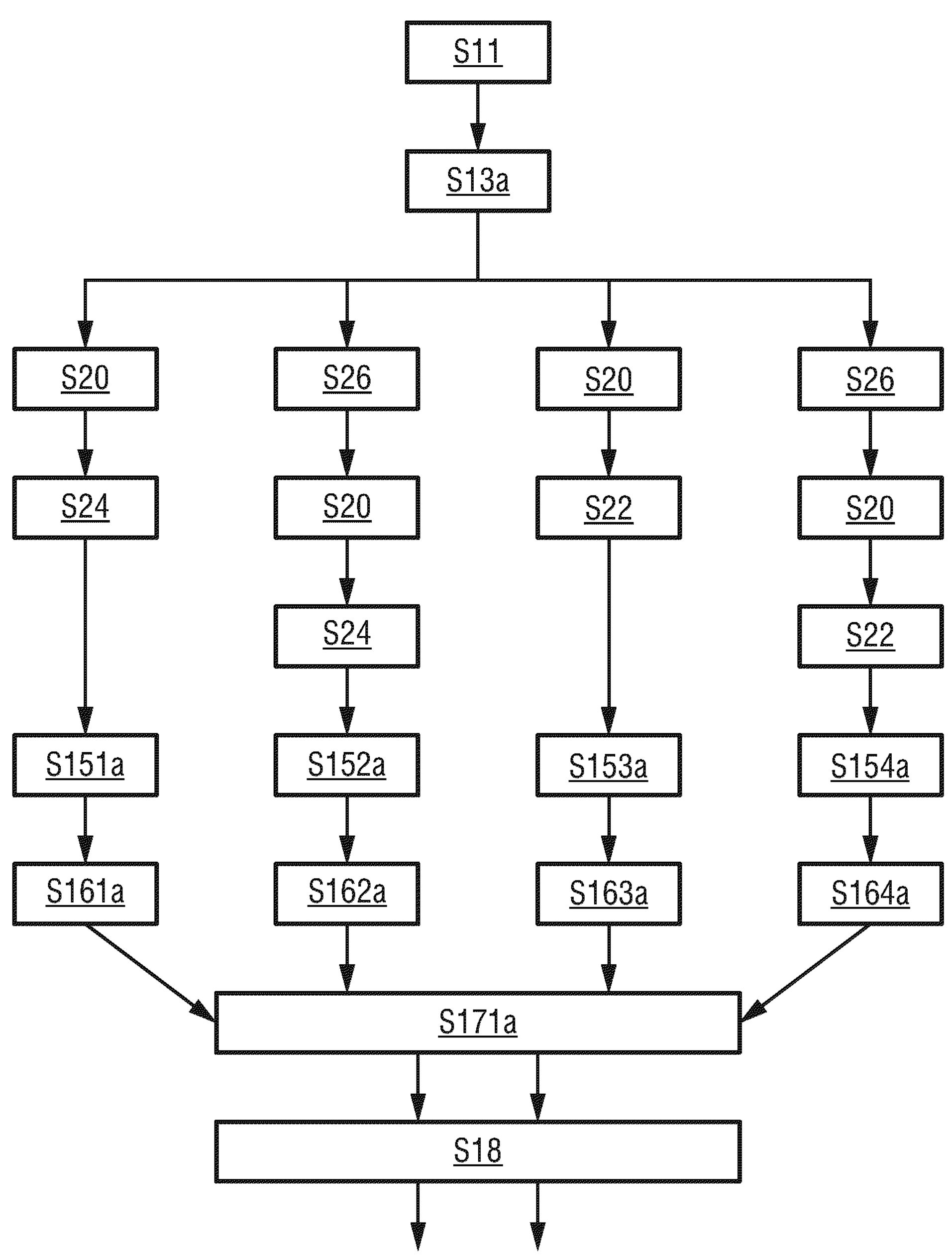
FIG. 6 shows a second schematic diagram of a method for determining a respiration rate of a subject according to the present invention.

FIG. 6 shows a second diagram of a method for determining a respiration rate of a subject. In a first step S11 of the method a PPG signal is provided from which in step S13*a* a sequence of features is extracted and a first feature signal is generated. The features signal is then processed in four different ways.

In a first way the first feature signal is resampled in step S20 and Fourier transformed in step S24. In parallel, i.e. in a second way, the first derivative of the first feature signal is calculated in step S26, the derivative is resampled in step S20 and the resampled derivative is Fourier transformed in step S24. In a third way, the first feature signal is resampled in step S20 and later on filtered in step S22. In a fourth way, the first derivative of the first feature signal is derived (step S26), which is then resampled (step S20) and filtered (step S22). Accordingly, there are two signals in the frequency domain and two signals in the time domain. From these signals, first respiration rates are extracted in steps S151*a*, S152*a*, S153*a* and S154*a*, respectively. From the signals in the frequency domain there may be extracted even more respiration rates. For example, from each signal in the frequency domain there may be extracted three respiration rates. To the extracted respiration rates there is then assigned a score in steps S161*a*, S162*a*, S163*a* and S164*a*. Subsequently, in step S171*a* similar respiration rates are grouped in respective groups and the scores of the respiration rates in a group are summed up to so called group scores. In this embodiment there are generated two groups, wherein a first group comprises respiration rates with a high likelihood to represent the true respiration rate, and wherein a second group comprises respiration rates with a low likelihood. In step S18, depending on the groups' composition (i.e. the number of respiration rates in a group) and/or the group scores and/or the scores of the different respiration rates in a group, it is decided which is the most probable and the second most probable respiration rate of the subject.

Figure 7:
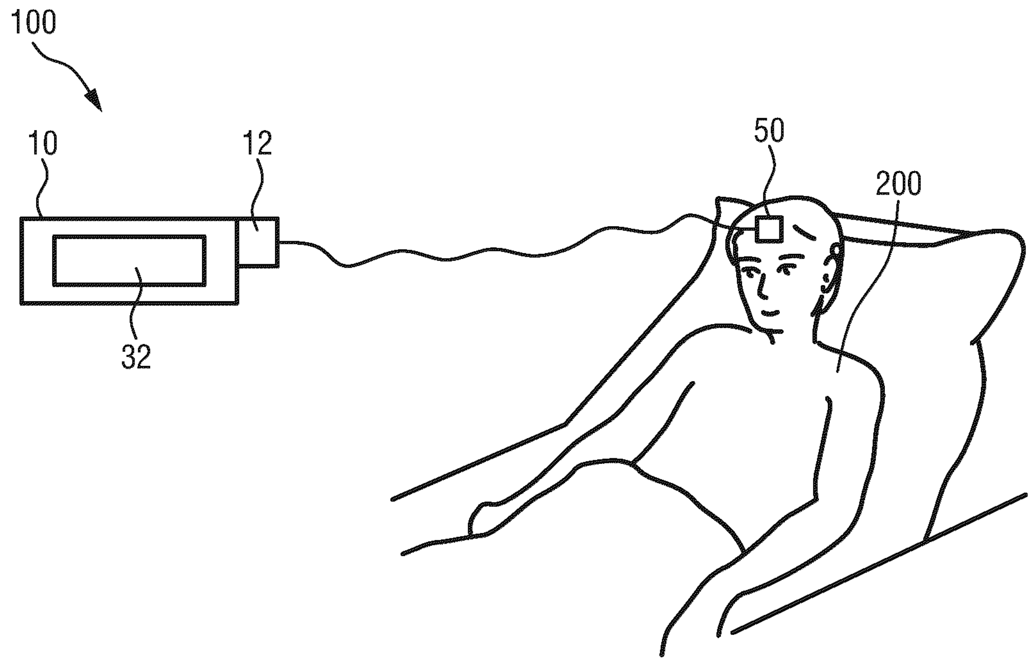
FIG. 7 shows a schematic diagram of an embodiment of a system for determining a respiration rate of a subject according to the present invention.

FIG. 7 shows a schematic diagram of an embodiment of a system for determining a respiration rate of a subject. The system 100 comprises a PPG sensor 50 configured to provide a red and/or infrared photoplethysmography, PPG signal, and a device 10 for determining a respiration rate of a subject 200. The device 10 of the system comprises an input interface 12, a feature signal unit 14, an extraction unit 16, an analyzing unit 18 and a display unit 32.

The PPG sensor 50 in this embodiment is designed in the form of a patch attached to the subject's forehead. Still, the PPG sensor 50 may also be attached to other body regions of the subject 200. In fact, it is also possible to use a remote PPG sensor. The sensor 50 and the input interface 12 of the device 10 are connected in a wired manner, however, the PPG sensor 50 and the input interface 12 may also work via a wireless communication interface.

The PPG sensor 50 is configured to measure a PPG signal of the patient and to provide said signal 11 to the input interface 12 of the device 10. The device 50 processes the PPG signal 11 and the analyzing unit 18 of the device 10 is configured to determine a most probable respiration rate 17 of the subject 200. The most probable respiration rate 17 is then displayed on the display unit 32 of the device 10. This way, clinical staff, for example, can recognize clinical deterioration early on.

Figure 8A:
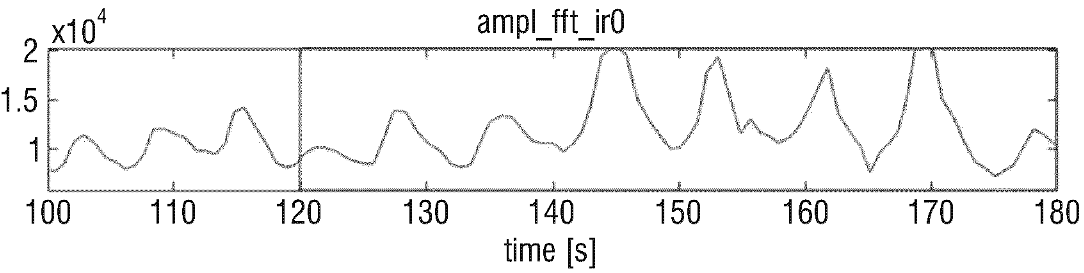
FIGS. 8A and 8B each show a diagram of a (second) feature signal according to the present invention.
Figure 8B:
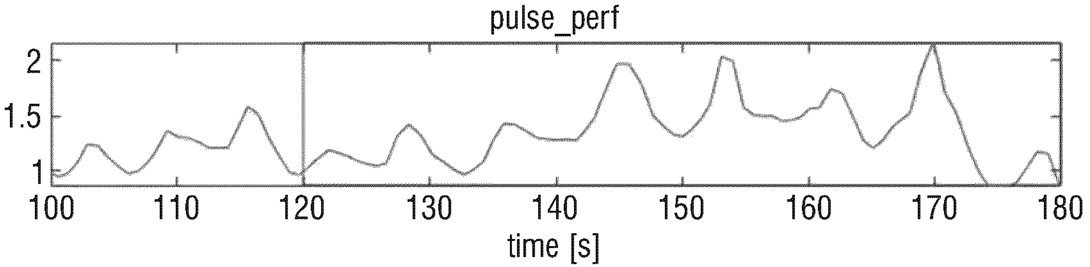

FIGS. 8A and 8B each show a diagram of a (second) feature signal according to the present invention. In particular, FIG. 8A shows a diagram of a sequence of amplitudes at the base frequency of each heart beat in the time domain and FIG. 8B shows a diagram of a sequence of single pulse perfusions in the time domain. In an exemplary embodiment, both features may be analyzed for 60 seconds as marked in the diagram.

Figure 9A:
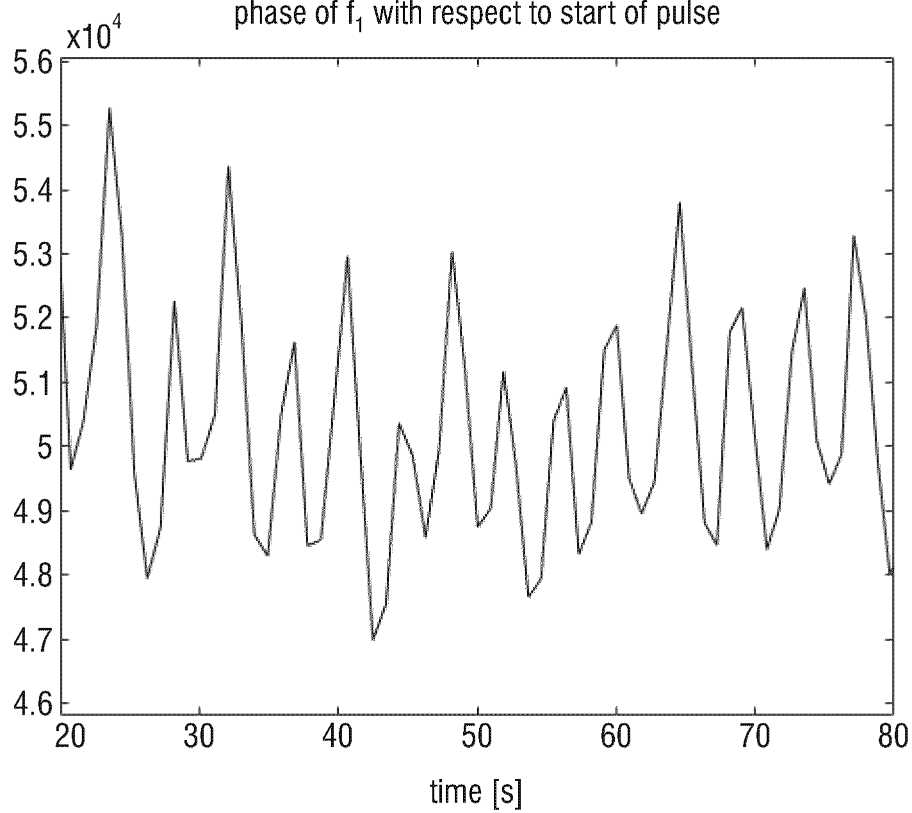
FIGS. 9A and 9B each show a diagram of a feature signal according to the present invention.
Figure 9B:
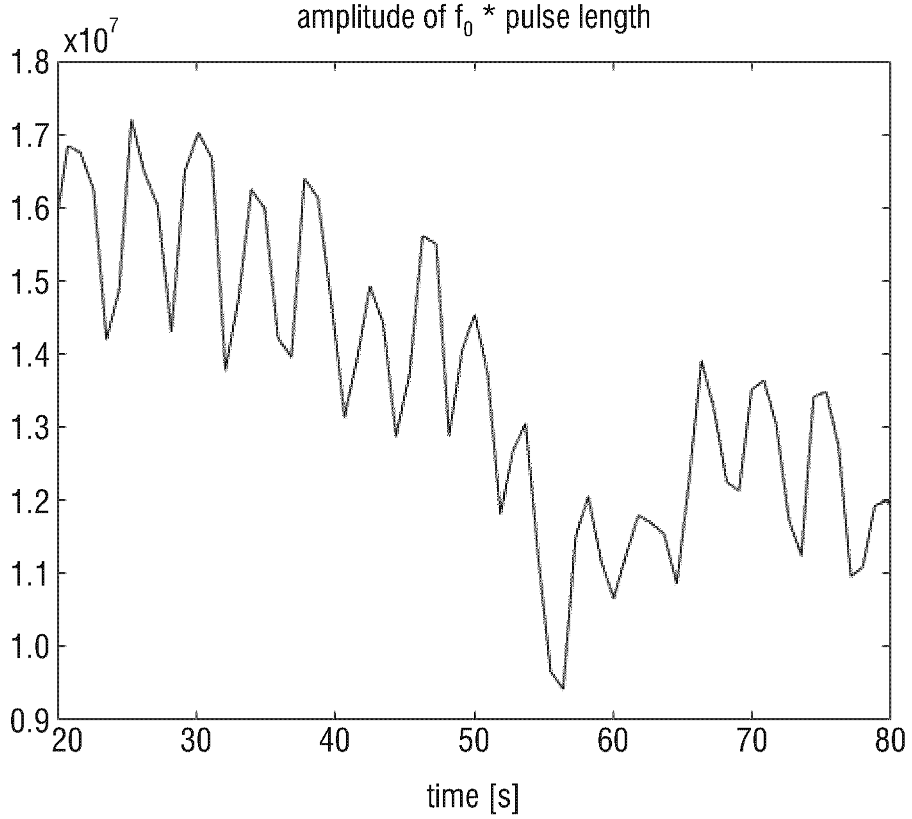

FIGS. 9A and 9B each show a diagram of a feature signal according to the present invention. In particular, FIG. 9A shows a diagram of a sequence of phases of the first harmonic of a heart beat with respect to a start of the heart beat. FIG. 9B shows a sequence of amplitudes at the base frequency of a heart beat times pulse length.

Figure 10:
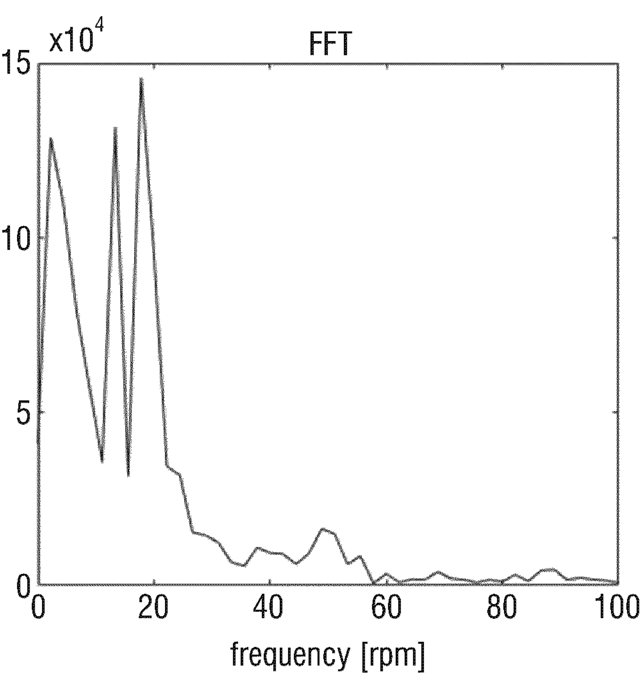
FIG. 10 shows a first diagram of an amplitude spectrum of the Fourier transform of the resampled features signal according to the present invention.

FIG. 10 shows a diagram of an amplitude spectrum of the Fourier transform of a resampled feature signal. Generally, from such a Fourier transform a (first or second) respiration rate may be derived. To derive the respiration rate (RR) a respiration rate range [minRR, maxRR] may be defined, in which the respiration rate is most probably located. The range may particularly depend on the pulse rate of the patient, which can also be extracted from the PPG signal (by the feature signal unit, for example). In an exemplary embodiment of the device the lower end of the range minRR may be defined by (pulse rate)/15 and the higher end of the range maxRR may be defined by (pulse rate)/2. However, other ranges may also be used. The highest peak in the range is then selected to be the respiration rate, i.e. the most probable respiration rate as calculated in this manner. The second highest peak is the second most probable respiration rate as calculated in this manner. The (most probable) respiration rates as calculated by different ways are then compared and a most probable respiration rate is determined by the analyzing unit 18. From the Fourier transform shown in FIG. 10, however, no respiration rates may be derived. In fact, no highest peak, marking a most probable respiration rate, can be inferred from the diagram shown. In fact, there are three peaks having almost the same height and hence no reliable respiration rate can be derived. In other words, to determine the score of a respiration rate there is determined the prominence of a peak in the diagram and the height of said peak. If for example, two peaks in the spectrum have a similar height, the determined respiration rate is not reliable and therefore has a small score. In the spectrum shown in FIG. 10 there are, in fact, three peaks of similar height. Therefore, the score of the corresponding respiration rates is quite low and the result therefore not reliable.

Figure 11:
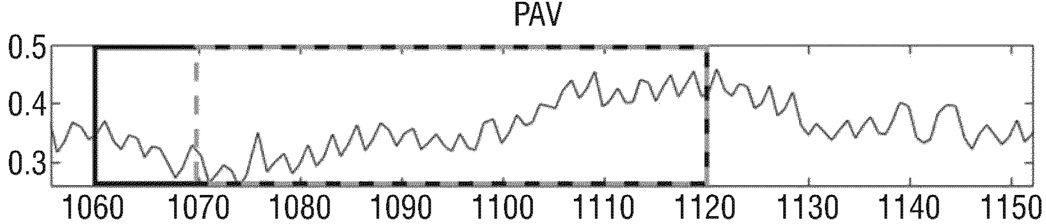
FIG. 11 shows a diagram of a pulse amplitude variability (PAV) in the time domain according to the present invention.

FIG. 11 shows a diagram of a pulse amplitude variability (PAV) in the time domain. There is marked a 60-seconds-window and a 50-seconds-window. Depending on the score corresponding to a (first or second) respiration rate as determined by the extraction unit 16, the time window may be adapted. In particular, if the score of the respiration rate for a time window of 60 seconds is small (and hence the respiration rate derived is not reliable), the time window may be reduced to 50 seconds, for example.

Figure 12:
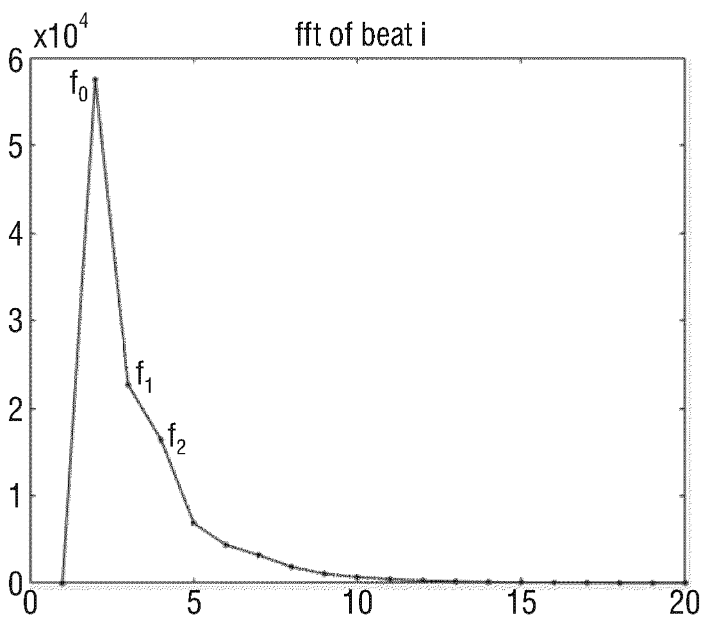
FIG. 12 shows a second diagram of an amplitude spectrum of the Fourier transform of a processed PPG signal corresponding to a single beat according to the present invention.

FIG. 12 shows a diagram of an amplitude spectrum of the Fourier transform of a single beat of an infrared raw wave. From this Fourier transform the base frequency and the harmonics may be derived. In particular, there are marked the base frequency (f0), the first harmonic (f1) and the second harmonic (f2) in FIG. 12. Accordingly, from such Fourier transform there may be derived the amplitude at the base frequency or the phase of the first harmonic. To obtain these values the following procedure is followed. First of all, all red or infrared raw wave PPG samples are taken from the beginning to the end of a single beat. Subsequently, there is subtracted a straight line, which is a fit through the first and last sample of the beat. Then, the Fourier transform of this signal corresponding to a single beat is calculated. In case the sample rate is 125 Hz and the valid pulse-rate-range is 29.3 to 300 beats per minute, the number of samples of a single beat varies between 25 and 256 samples. Accordingly, the number of points in the Fourier transform may vary with the length of pulses.

Figure 13:
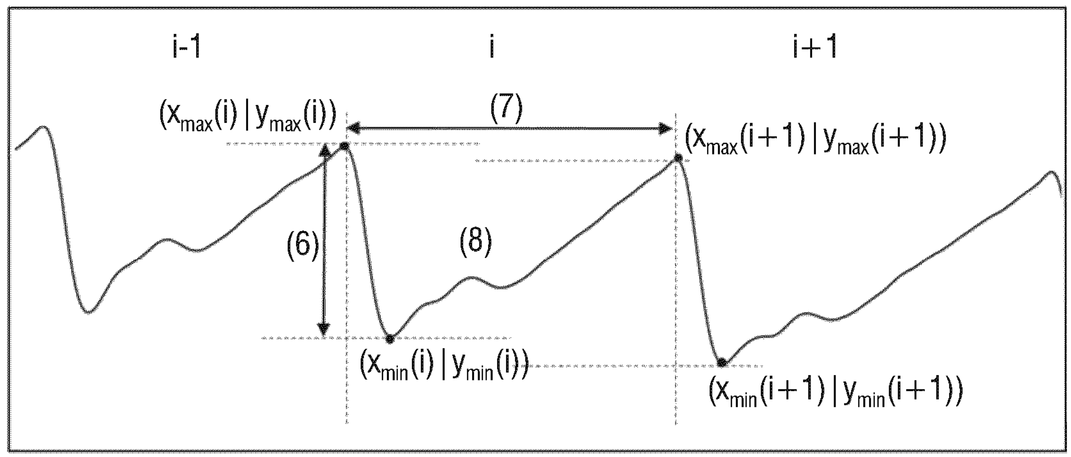
FIG. 13 shows a diagram of a beat-to-beat signal as derived from an infrared and/or red PPG signal showing different features of a beat according to the present invention.

FIG. 13 shows a diagram of a beat-to-beat signal as derived from an infrared and red PPG signal showing different features of a beat. In particular, FIG. 13 shows three beats originating from an infrared raw wave. The surface of beat i is defined as the area spanned between the raw signal and a straight line from the maximum of said beat to the maximum of the following beat i+1. FIG. 13 further shows the features PAV, i.e. the heights of the pulses, and PWV, i.e. the widths of the pulses.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for determining a respiration rate of a subject, comprising:
- an input interface configured to be connected with a photoplethysmography (PPG) sensor for obtaining a red and/or an infrared PPG signal while the PPG sensor is worn by or attached to the subject; and
- a processor comprising;
  - a feature signaler configured to extract a first sequence of features from the PPG signal and to generate a first feature signal from said sequence of features;
  - a resampler configured to resample with a resampling function the first feature signal to yield a resampled signal with a constant sampling rate and/or to resample a first derivative to yield a resampled first derivative with a constant sampling rate;
  - a transformer configured to calculate a Fourier transform of the resampled signal to yield a transformed resampled signal or to calculate a Fourier transform of the resampled first derivative to yield a transformed resampled first derivative; and
  - an extractor configured to extract from the transformed resampled signal a first respiration rate or from the transformed resampled first derivative the first respiration rate;
- wherein the first sequence of features is a sequence of phases of the first harmonic of a heart beat of the subject with respect to a start of the heart beat and wherein the first feature signal corresponds to the sequence of phases.

2. The device of claim 1, where the processor further comprises an analyzer, the extractor configured to extract from the transformed resampled signal at least one further first respiration rate and wherein the analyzer is configured to determine from the at least two first respiration rates a most probable respiration rate.

3. The device of claim 2, the processor further comprising a scorer configured to assign a score to the at least first two respiration rates describing the probability of the first respiration rates to represent the true respiration rate of the subject, wherein the analyzer is configured to determine the most probable respiration rate using said scores.

4. The device of claim 2, the processor further comprising a grouper configured to group the at least two first respiration rates into groups of similar respiration rates, wherein similarity is assumed if respiration rates differ by less than a predetermined rate difference.

5. The device of claim 4, wherein the grouper is further configured to add the scores of the at least two first respiration rates in a group to yield a group score, wherein the analyzer is configured to determine the most probable respiration rate from the group with the highest group score.

6. The device of claim 5, wherein the analyzer is further configured to determine a confidence value for the most probable respiration rate based upon the number of respiration rates and the group score of the corresponding group.

7. The device of claim 4, wherein said predetermined rate difference is no more than two respirations per minute.

8. The device of claim 1,
- wherein the feature signaler is configured to extract a second sequence of features from the PPG signal and to generate a second feature signal from said second sequence of features;
- wherein the extractor is configured to extract from the second feature signal at least a second respiration rate; and
- wherein the second feature signal corresponds to at least one of the following: (a) an amplitude at the base frequency of the subject's heart beats times pulse width of the heart beats, (b) an amplitude at the base frequency of the heart beat, (c) single pulse perfusion, (d) pulse rate, (e) amplitude ratio of the base frequency and the first harmonic of the beat, (f) pulse amplitude variability, (g) pulse width variability, or (h) surface of the beat.

9. The device of claim 1, further comprising a calculator configured to calculate the first derivative of the first feature signal.

10. The device of claim 1, further comprising a filter configured to filter the resampled signal to yield a filtered resampled signal wherein the extractor is configured to extract from the filtered resampled signal the first respiration rate, and/or to filter the resampled first derivative to yield a filtered resampled first derivative, wherein the extractor is configured to extract from the filtered resampled first derivative the first respiration rate.

11. The device of claim 10, wherein the filter is configured to filter adaptively in accordance with an expected respiration rate corresponding to the resampled signal or the resampled first derivative.

12. A computer-implemented method for determining a respiration rate of a subject using a device in communication with a photoplethysmography (PPG) sensor, comprising:
- obtaining, from the PPG sensor via an input interface of the device, a red and/or infrared PPG signal;

extracting a first sequence of features from the PPG signal and generating a first feature signal from said sequence of features;

resampling with a resampling function the first feature signal to yield a resampled signal with a constant sampling rate and/or to resample a first derivative to yield a resampled first derivative with a constant sampling rate;

calculating a Fourier transform of the resampled signal to yield a transformed resampled signal or to calculate a Fourier transform of the resampled first derivative to yield a transformed resampled first derivative; and extracting from the transformed resampled signal a first respiration rate or from the transformed resampled first derivative the first respiration rate;

wherein the first sequence of features is a sequence of phases of the first harmonic of a heart beat of the subject with respect to a start of the heart beat and wherein the first feature signal corresponds to the sequence of phases.

13. The computer-implemented method of claim 12, further comprising:

grouping the at least two first respiration rates into groups of similar respiration rates, wherein similarity is assumed if respiration rates differ by less than a predetermined rate difference.

14. The computer-implemented method of claim 13, wherein said predetermined rate difference is no more than two respirations per minute.

15. The computer-implemented method of claim 13, further comprising:

adding the scores of the at least two first respiration rates in a group to yield a group score, wherein the analyzer is configured to determine the most probable respiration rate from the group with the highest group score.

16. A non-transitory computer-readable medium that stores therein a computer program product, which, when executed on a processor, causes the processor to:

obtain a red and/or infrared photoplethysmography (PPG) signal;

extract a first sequence of features from the PPG signal and generating a first feature signal from said sequence of features;

resample with a resampling function the first feature signal to yield a resampled signal with a constant sampling rate and/or to resample a first derivative to yield a resampled first derivative with a constant sampling rate;

calculate a Fourier transform of the resampled signal to yield a transformed resampled signal or to calculate a Fourier transform of the resampled first derivative to yield a transformed resampled first derivative; and extract from the transformed resampled signal a first respiration rate or from the transformed resampled first derivative the first respiration rate;

wherein the first sequence of features is a sequence of phases of the first harmonic of a heart beat of the subject with respect to a start of the heart beat and wherein the first feature signal corresponds to the sequence of phases.

17. The non-transitory computer-readable medium of claim 16, wherein the processor is further caused to:

group the at least two first respiration rates into groups of similar respiration rates, wherein similarity is assumed if respiration rates differ by less than a predetermined rate difference.

18. The non-transitory computer-readable medium of claim 16, wherein said predetermined rate difference is no more than two respirations per minute.

19. The non-transitory computer-readable medium of claim 17, wherein the processor is further caused to:

add the scores of the at least two first respiration rates in a group to yield a group score, wherein the analyzer is configured to determine the most probable respiration rate from the group with the highest group score.

* * * * *